(12) United States Patent
Lipp

(10) Patent No.: US 6,391,628 B1
(45) Date of Patent: May 21, 2002

(54) DIGESTER WITH AGITATOR AND METHOD FOR OPERATING AN AGITATOR IN A DIGESTER

(76) Inventor: Xaver Lipp, Hohenstaufenstrasse 30, D-73479 Ellwangen (DE)

(*) Notice: Subject to any disclaimer, the term of this patent is extended or adjusted under 35 U.S.C. 154(b) by 0 days.

(21) Appl. No.: 09/554,413

(22) PCT Filed: Oct. 14, 1998

(86) PCT No.: PCT/EP98/06515

§ 371 Date: May 12, 2000

§ 102(e) Date: May 12, 2000

(87) PCT Pub. No.: WO99/32600

PCT Pub. Date: Jul. 1, 1999

(30) Foreign Application Priority Data

Dec. 18, 1997 (DE) .......................... 197 56 485
Mar. 16, 1998 (DE) .......................... 198 11 398

(51) Int. Cl.$^7$ .................................. C12M 1/02
(52) U.S. Cl. ...................... 435/295.1; 435/300.1; 435/262; 366/262; 366/270
(58) Field of Search .................. 435/289.1, 295.1, 435/262, 280.2, 290.4, 300.1; 366/262, 270; 210/603, 167; 71/8–10

(56) References Cited

U.S. PATENT DOCUMENTS 2,522,281 A * 9/1950 Koskinen
3,635,796 A   1/1972 Imada et al.
5,658,076 A * 8/1997 Crump et al.

FOREIGN PATENT DOCUMENTS

| DE | 4302740 A1 | 8/1984 |
| DE | G9404188.1 | 7/1994 |
| DE | 19621914 C1 | 8/1997 |
| GB | 687296 | 2/1953 |
| JP | 59 228998 A | 12/1984 |
| SU | 181039 | 5/1965 |
| WO | 82/00299 | 2/1982 |

* cited by examiner

Primary Examiner—William H. Beisner
(74) Attorney, Agent, or Firm—Roylance, Abrams, Berdo & Goodman, L.L.P.

(57) ABSTRACT

A digester with an agitator and a method of operating an agitator in a digester can be used, for instance, in agricultural biogas plants and communal clarification plants. The digester with an agitator and the method feature improved mixing of the waste products in the digester and enhanced digester efficiency. The digester includes a preferably round bottom surface, a filler rod and an agitator with a drive axle, preferably arranged on the periphery of the digester. The agitator is mounted in a stirring shaft or stirring pipe arranged underneath the filler standard. The method for operating the agitator in a digester involves stirring the content while material is fed into the digester through the filler standard.

20 Claims, 4 Drawing Sheets

DIGESTER WITH AGITATOR AND METHOD FOR OPERATING AN AGITATOR IN A DIGESTER

FIELD OF THE INVENTION

The present invention relates to a digester with an agitator and an associated method for the operation of an agitator in a digester. The agitator is arranged in a stirring shaft or pipe and has a drive axle.

BACKGROUND OF THE INVENTION

A digester with an agitator in a stirring shaft or pipe is conventionally used in agricultural biogas plants and communal clarification plants. In such digester, organic waste materials remain, on the average, for a few days at a temperature above atmospheric temperature, for example at approximately 35° C. The agitator provided in the digester, among other things, serves to distribute waste materials introduced through a filling standard support arrangement. The agitator is operated in timed cycles, so that an optimum temperature balance prevails throughout the digester and the newly introduced waste materials are distributed uniformly in the digester. Through this arrangement, the agitator serves to supply the bacteria contained in the digester regularly with nutrients, to prevent the formation of layers, especially to destroy floating and sinking layers which are forming continually, and to release the gas bubbles which are bound on sludge particles in deeper layers. Gas separation occurs during the fermenting process in the digester, whereby the biogas being generated can be collected in a storage container.

A mixing device for liquid-filled containers is disclosed in DE 94 04 188 U1. In this case, a circulating device connected immovably with a guide assembly is lowered and raised inside and along the container and outside of a guide pipe fastened on the bottom of the container. The spacing between the guide pipe and the wall of the container is selected to be of such dimensions that the circulating device includes the open chambers or free spaces on the suction side and radially which are required for its undisturbed operation.

WO 82/00299 discloses a ball-shaped digester with a helical screw pump arranged in a central pipe shaft and having a vertically running drive axle. The pipe shaft projects upward out of the digester, and includes a partition sealing the top part of the pipe shaft from the gas chamber of the digester. At the level of the equator of the ball or sphere, forming the fill level of the digester, the pipe shaft has a plurality of openings through which the screw pump suctions the material to be pumped. A filling pipe is built into the top part of the pipe shaft, through which material is to be fed into the digester.

A mixing device for liquid-filled containers is disclosed in DE 94 04 188 U1. A circulating device is securely connected with a guide assembly and is raised and lowered by means of a lifting device in the container, along and to the exterior of a guide pipe fastened on the bottom of the container. The distance between the guide pipe and the wall of the container is of such dimensions that the circulating device incorporates radial free spaces on the suction side required for its undisturbed function.

SUMMARY OF THE INVENTION

Objects of the present invention are to provide a digester having an agitator as well as a method for the operation of an agitator in a digester, which digester and method offer an improved thorough mixing of the waste materials in the digester, and therefore, increase the efficiency of the digester. Additionally, the gas separation is particularly improved as a result of an improved thorough mixing of the waste materials.

The foregoing objects are attained by a digester having with a bottom surface and its agitator is accommodated in a stirring conduit arranged beneath the filling standard inlet. The extended projection of the driving or stirring axle of the agitator intersects the periphery of the digester forming a secant thereof. In other words, the extended projection is not directed precisely to the midpoint of the digester.

The configuration of the digester generally involves a cylindrical, closed container, preferably with a circular bottom surface. The bottom surface, however, can have basically any desired contour. Rounded corners or a circular shape are advantageous because these configurations require the generation of rotary movement of the waste materials in the digester. In addition to a driving axle, the agitator also has one or more agitator blades or an agitation or stirring screw. The agitator is preferably mounted on the periphery or edge of the digester. Through the filling inlet, new waste materials are fed into the digester. The stirring pipe generally runs perpendicular and extends preferably as far as a distance of from 0.2 m to 1 m beneath the relevant filling level.

The agitator is generally arranged in a bent, horizontal segment of the stirring pipe, whereby the driving axle extends preferably in the middle and axially parallel to the horizontal segment of the stirring pipe. Alternatively, the agitator can be arranged to the exterior of the stirring pipe, but directly beneath its bottom end. Then, the driving axle of the agitator is not directly to the midpoint of the digester, but rather the extended driving axis intersects the periphery or the edge or the contour of the digester forming a secant.

Advantageously, a rotary or rotary agitating movement of the waste materials in the digester is attained. This rotary movement leads to an especially beneficial thorough mixing of the waste materials, and thus, to increased efficiency of the digester with regard to the development of gases. The arrangement of the agitator beneath the filling inlet provides the advantage that newly filled-in material is suctioned directly into the stirring pipe and then is mixed especially effectively with the waste materials found already in the digester. As a result of the arrangement of the present invention providing the stirring pipe beneath the filling inlet, the development of floating layers is effectively avoided by means of newly introduced waste materials.

When a certain distance is maintained between the agitator and the bottom of the digester, a sediment of digested waste materials can be formed on the bottom of the digester, where it is not whirlpooled up again by the agitation movement. Thus, any undesired mixing of the still gas-producing waste materials with the no longer gas-producing sediment in the bottom of the digester is effectively avoided. Finally, as a result of this, the efficiency of gas formation in the digester is further increased.

As a result of the height-adjustability of the agitator arrangement, the agitating or stirring effect can be set at various heights within the digester. This adjustment leads to an improved thorough mixing of the waste materials, and consequently, to increased efficiency of gas formation. The height adjustment can be executed either manually or mechanically, as well as together with the agitation or in some other relation to the agitation.

A sweeping or tilting of the driving axle out of the horizontal causes not only a horizontal rotary movement of the waste materials, but also a resulting thorough vertical mixing of the waste materials. The angle between the drive axis and the horizontal is preferably between 5° and 45°.

The motor unit can be arranged to the exterior of the digester, through the outwardly directed drive axis. This arrangement is advantageous especially with regard to maintenance work on the motor. By the provision of a gearing or transmission connection, different speed ratios, both faster and slower, and consequently, different rpm's of the agitator could be realized. The gearing or transmission connection can then also occur through a gear train. Preferably a chain connection or belt transmission is provided. A coupling, for example even a slip coupling, can be provided.

With the driving axle to the exterior of the digester as another drive shaft in addition to the main drive shaft for example through the electric motor, powering the drive is possible by means of a combustion engine, for example by a tractor. This agitating or stirring by means of a combustion engine allows for higher agitation or stirring performance, for example for the purpose of attaining a particularly effective thorough mixing of the waste materials in the digester or for cleaning purposes.

The length of the stirring pipe can be adapted to the particular liquid state in the digester. For this purpose, the length of the stirring pipe is preferably selected so that the distance from the top end of the stirring pipe to the surface of the liquid in the digester is nearly constant even with varying fill levels. With reference to the narrow width of the stirring pipe and the suction performance of the agitator, an optimum suction effect can be attained relating to the float layers forming on the surface. The space can be adjusted especially with reference to the consistency and/or viscosity of the liquid so that during the agitation process the liquid surface in the area of the stirring pipe can be lowered as with a funnel. Particularly, the clumps formed on the surface are optimally sucked in and dissolved by the agitation. The efficiency of the digester is thereby increased. Especially, the gas separation is improved by the improved thorough mixing of the waste materials.

The present invention is not limited to agitators for digesters. It can likewise be used for other purposes, for example, in a container with an agitator assembly for the production or processing of foods.

The stirring pipe can be embodied as a one-part or multi-part hollow cylindrical body. It can also be formed by form-locking cooperation of a metal sheet with the partition wall of the digester in such a manner that the metal sheet forms a part of the partition wall of the stirring pipe or stirring shaft and the partition wall of the digester forms the other part of the partition wall of the stirring pipe.

The stirring pipe can incorporate at least two telescopic sections sliding one into the other. The use of telescopic sections or sections of pipe allows a great length variation dependent upon the number of sections being used.

The top section of the pipe sections can have a rod-like lengthened portion projecting over the top edge upward from the top section of the pipe sections. This extension preferably projects beyond the surface of the liquid in the container and allows the operator of the digester to determine precisely the distance of the top edge of the stirring pipe from the liquid surface, even when the liquids are deeply clouded or opaque. A favorable value for this distance has been proven to be within a range of from 0.1 m to 1.0 m, and preferably between 0.15 m and 0.30 m. An alternative or a complement for the distance determination are ultrasound measurements, especially used in the area of clarification operations.

The sections of pipe can be provided with clamping or catch means for fixing of the individual sections of pipes with one another. Thus, a secure and infinitely variable length adaptation of the stirring pipe is attained.

A section of pipe, preferably the top section of pipe, can be coupled mechanically with a float, whereby the float floats on the surface of the liquid. Through the geometric dimensional configuration of the mechanical coupling between float and section of pipe, a constant distance is maintained between the top end of the stirring pipe and the liquid surface. The mechanical coupling can be realized, for example, by an aluminum rod. The rod is aligned in such a manner that it forms an angle of for example 30° with the horizontal and is aligned by the stirring pipe projecting out radially toward the midpoint of the filling container. Alternatively, a plurality of float bodies can be arranged on one or more rods or crosspieces.

By stirring the contents of the digester while waste material is in the process of being filled into the digester through the filling inlet or standard arrangement, a uniform and thorough mixing of new waste material with the waste material already in the digester is attained. This occurs especially because of the configuration of the digester of the present invention with the stirring pipe or shaft arranged beneath the filling standard. Thus, homogenization of the waste materials found in the digester is produced, and with that, the efficiency of the gas formation is increased.

The direction of flow in the stirring pipe can be reversed by stirring in reverse direction of rotation to clean stirring pipe. Especially the fiber material in the stirring pipe collected at the end of the suction pipe is dissolved and rinsed out. In normal operation, such fiber material would disturb and misalign the suction side of the stirring pipe.

Other objects, advantages and salient features of the present invention will become apparent form the following detailed description, which, taken in conjunction with the annexed drawings, discloses preferred embodiments of the present invention.

BRIEF DESCRIPTION OF THE DRAWINGS

Referring to the drawings which form a part of this disclosure.

DETAILED DESCRIPTION OF THE INVENTION

Figure 1:
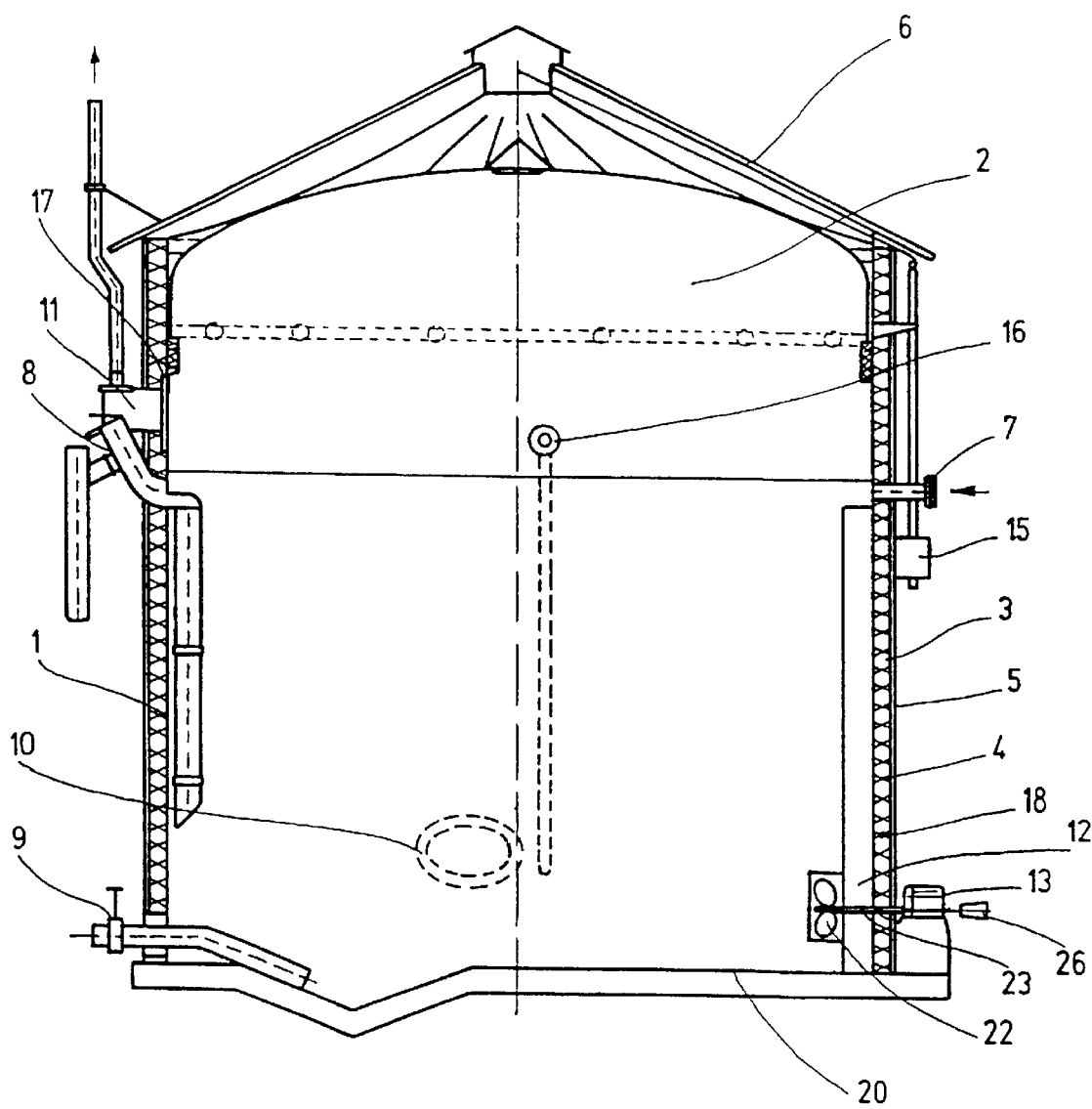
FIG. 1 is a side elevational view in section of a digester according to a first embodiment of the present invention.

FIG. 1 shows a side elevational view of the digester 1 according to the present invention. The illustrated digester 1 forms a biogas reactor with integrated gas storage hood 2. Digester 1 is in the form of a cylindrical, closed chamber with a circular bottom surface 20 and provided with a roof 6. Digester 1 has insulation 3 around the outside, embodied as a wall heating arrangement or heater 4 which has an outside covering 5. Fresh substrates or fresh waste materials are fed in through filling standard or inlet 7. The discharge 8 incorporates an integral emergency discharge. Digester 1 is emptied through the attachment 9 which can be blocked off. Digester 1 also has a manhole 10. An assembly 11 aids in controlling both the high-pressure and vacuum-pressure in gas storage hood 2.

Figure 2:
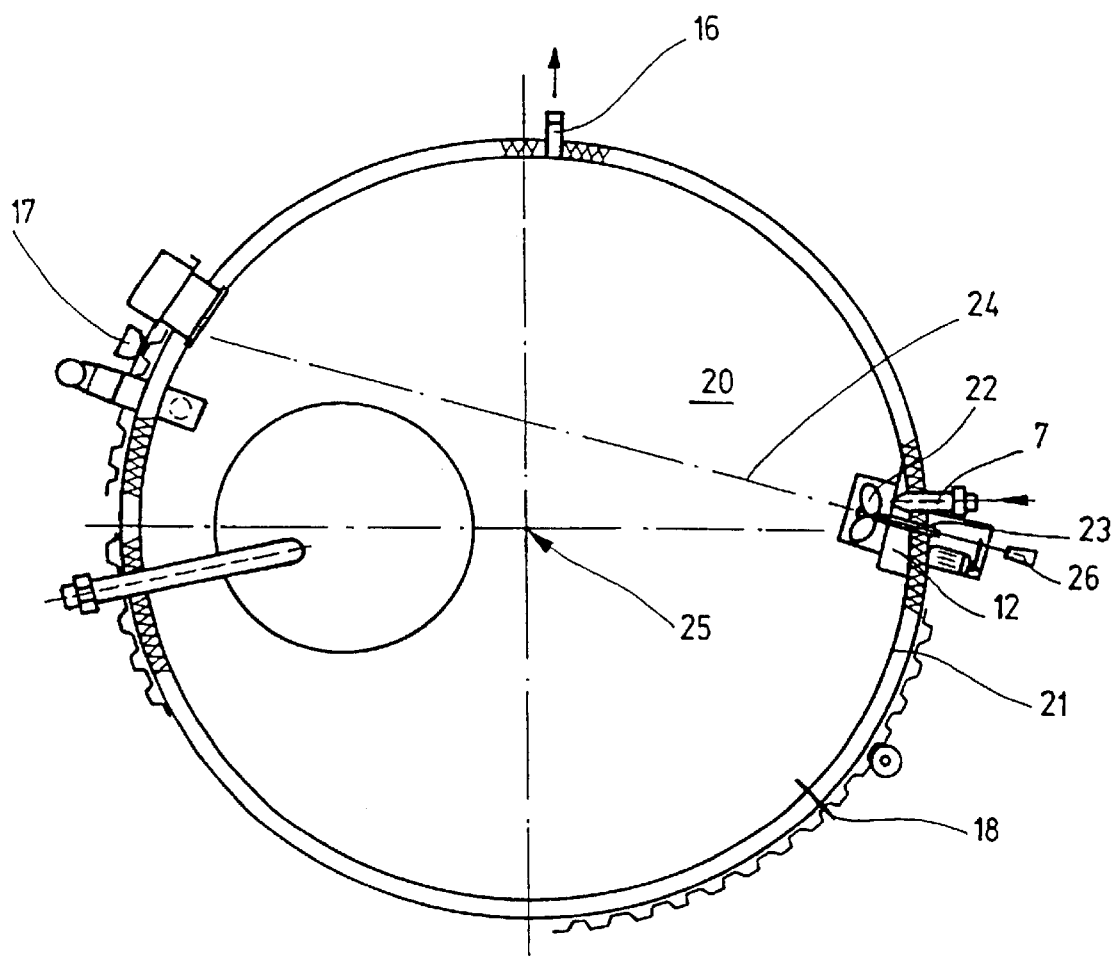
FIG. 2 is a top plan view in section of the digester of FIG. 1.

On the periphery or edge 21 of digester 1, as in FIG. 2, an agitator 22 with a driving axle 23 is arranged. The agitator can be powered by a drive transmission 13 to cause homogenization of the waste materials found in digester 1. Drive transmission 13 is formed by an electric motor coupled with driving axle 23 through a transmission connection including sprocket wheel arrangements and a drive chain. Agitator 22 includes a multi-bladed agitating screw.

Agitator 22 is located in a horizontal segment of stirring pipe or conduit 12. The main body of the stirring pipe is mounted vertically in its length extension, with stirring pipe 12 being arranged at the edge 21 of digester 1. Stirring pipe 12 extends as far as 0.2 m to 1 m below the fill level of waste materials in digester 1. The width or diameter of stirring pipe 12 at its narrowest can be between 0.5 m and 1.5 m.

Driving axle 23 extends horizontally. Alternatively, the driving axle can be tilted at an angle of between 0° and 90°, relative to the horizontal. Preferably it is at an angle between 5° and 45°. The tilting can be adjustable.

Stirring pipe 12 rests on the bottom surface 20 of digester 1. Alternatively, it can also end at some distance above bottom surface 20. Agitator 22 is at some distance from the bottom of the digester, for example, at a distance of between 0.5 m and 1 m from the bottom 20 of digester 1.

Digester 1 also ahs a gas volume indicator 15 as well as an attachment 16 for gas removal. Furthermore, an attachment 17 for desulfurization and an attachment 18 for temperature measurement of the waste material found in digester 1 are provided.

FIG. 2 shows a plan view of digester 1 as in FIG. 1. The extended projection 24 of driving axle 23 in the horizontal plane of bottom surface 20 intersects the periphery or peripheral wall 21 of digester 1 forming a secant-like configuration. Driving axle 23 is therefore not axially aligned with midpoint or center 25 of digester 1. Stirring pipe 12 is configured to be triangular, whereby two arms of the triangle form a right angle and the hypotenuse or third arm is formed by a segment of the periphery 21 of digester 1. Agitator 22 is accommodated in a horizontal segment of stirring pipe 12, and is arranged directly beneath filling standard 7.

Figure 3:
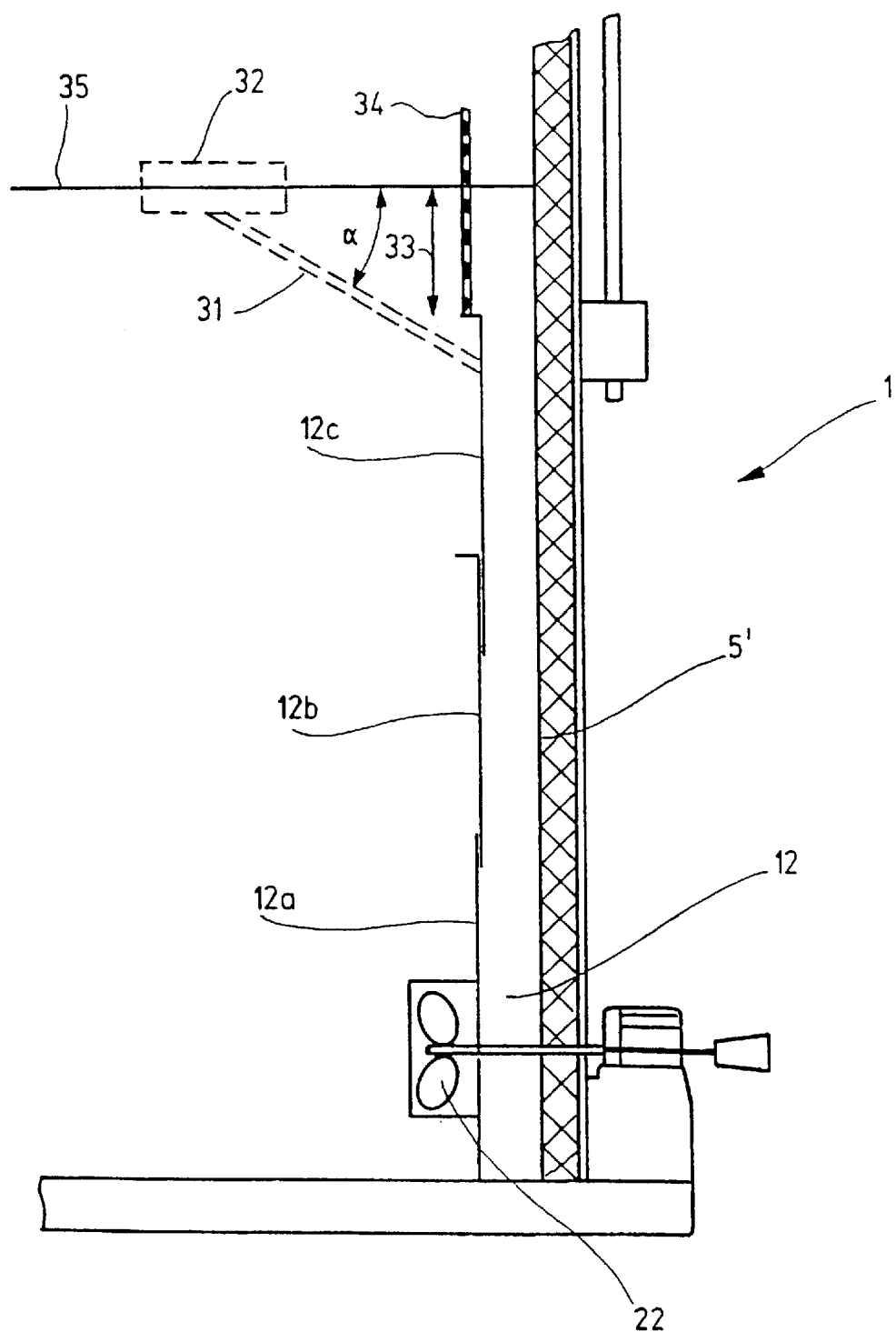
FIG. 3 is an enlarged, partial side elevational view in section of a digester according to a second embodiment of the present invention with a telescoping stirring pipe.

FIG. 3 shows an enlarged section of a digester similar to that of FIG. 1, with a stirring pipe 12 configured to be telescopic. Stirring pipe 12 in this case is embodied to be a part of the partition wall 5' of digester 1, as well as being embodied in three partial sections of pipe 12a, 12b and 12c. These pipe partial sections are configured to slide telescopically one within the other. A float 32 is fastened by means of a rod 31 on top section of pipe 12c. Rod 31 forms an angle alpha of approximately 30° with the liquid surface 35. A constant distance 33 is guaranteed between top section of pipe 12c and liquid surface 35 by means of the geometric construction of the mechanical coupling of top section of pipe 12c with float 32 by means of rod 31. This distance 33 is preferably between 0.15 m and 0.30 m.

Filling standard 7 is not shown in the cross section of FIG. 3. Filling standard 7 can also be arranged, for example, at any desired point on digester 1. As in the earlier described embodiment, agitator 22, in relation to the vertical arrangement, is arranged beneath filling standard 7. Also, the top edge of top section of pipe 12c preferably lies beneath filling standard 7.

As a result of the use of the illustrated float 32, no clamp and catch means is required. Alternatively to float 32, or even in addition thereto, commercially available clamping or catching means could be provided for the fixing of the length of stirring pipe 12. Alternatively or in addition to float 32, a rod-like extension 34 can also be mounted on top section of pipe 12c. Extension 34 projects slightly beyond the surface of liquid surface 35, and indicates to the operator of the digester the distance 33 of top section of pipe 12c from liquid surface 35, even in case of cloudy or opaque liquids.

Figure 4:
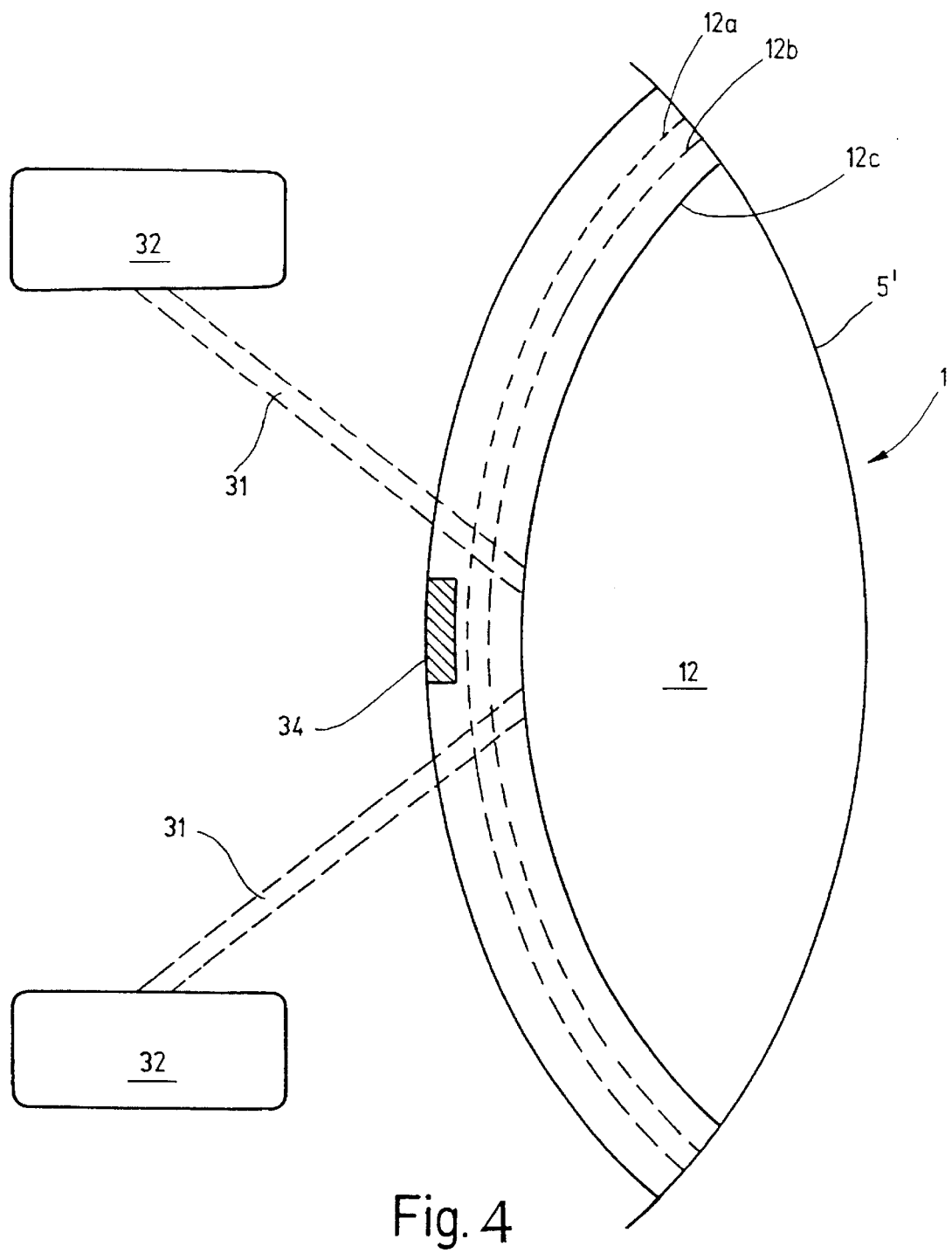
FIG. 4 is a top plan view in section of the digester of FIG. 3.

FIG. 4 shows a cutout section of the plan view of digester 1 of FIG. 3. Two float bodies 32 are fastened to two rods 31 on the top section of pipe 12c. In the plan view, the two rods 31 in the horizontal plane form an angle of approximately 90°. With this arrangement of float bodies 32, the suction of floating layers is prejudiced neither along the periphery of digester 1 nor from the middle of digester 1. Stirring pipe 12, in the present case, is formed partially by partition wall 5' of digester 1 and partially by the elliptical partial pipe segments 12a, 12b and 12c. Also, the rod-like extension 34 extending perpendicular to the plane of the drawing can be recognized in the plan view of the drawing.

While various embodiments have been chosen to illustrate the invention, it will be understood by those skilled in the art that various changes and modifications can be made therein without departing from the scope of the invention as defined in the appended claims.

What is claimed is:

1. A digester, comprising:
   a filling inlet;
   a bottom surface;
   a peripheral wall extending from said bottom surface;
   a stirring conduit located adjacent to and within said peripheral wall and beneath said filling inlet; and
   an agitator arranged in said stirring conduit and adjacent said peripheral wall and having a drive axle, and said drive axle having an extended projection intersecting said peripheral wall in a horizontal plane forming a secant of said peripheral wall.

2. A digester according to claim 1 wherein
   said bottom surface is round.

3. A digester according to claim 1 wherein
   said agitator is spaced by a distance from said bottom surface.

4. A digester according to claim 1 wherein
   said stirring conduit is triangular in transverse cross section.

5. A digester according to claim 1 wherein
   said stirring conduit is partially elliptical in transverse cross section.

6. A digester according to claim 1 wherein
   said agitator is coupled to a tackle for adjusting a height thereof in the digester.

7. A digester according to claim 6 wherein
   said tackle is a line tackle.

8. A digester according to claim 6 wherein
   said tackle is a chain tackle.

9. A digester according to claim 1 wherein
   said drive axle forms an angle of 0° to 90° with a horizontal line.

10. A digester according to claim 1 wherein
    said drive axle extends to an exterior of said peripheral wall where said drive axle is coupled to a transmission connection.

11. A digester according to claim 10 wherein said transmission connection is coupled to an electric motor.

12. A digester according to claim 10 wherein said drive axle is located outside of said peripheral wall.

13. A digester according to claim 1 wherein said stirring conduit is adjustably variable in length in a vertical direction.

14. A digester according to claim 1 wherein said stirring conduit comprises at least two partial pipe sections telescopically connected.

15. A digester according to claim 14 wherein one of said partial pipe section comprises a top pipe section having a rod extension at a top end thereof, said rod extension extending upwardly and having a length between 0.1 meter and 1.0 meter.

16. A digester according to claim 15 wherein said length of said rod extension is between 0.15 meter and 0.30 meter.

17. A digester according to claim 14 wherein said partial pipe sections comprise clamping means.

18. A digester according to claim 14 wherein one of said partial pipe sections is mechanically coupled to a float.

19. A method of operating a digester, comprising the steps of:

dispensing contents from a filling inlet into a stirring conduit located adjacent to and within a peripheral wall extending from a bottom surface of the digester and located beneath the filling inlet; and stirring the contents in timed cycles while the contents are filled into the stirring conduit through the filling inlet by an agitator arranged in the stirring conduit and adjacent the peripheral wall, the agitator having a drive axle with an extended projection intersecting the peripheral wall in a horizontal plane forming a secant of the peripheral wall.

20. A method according to claim 19 wherein the stirring conduit is cleaned by stirring in a reverse rotary direction in timed cycles of one day to one week.

* * * * *